US007787943B2

(12) United States Patent
McDonough

(10) Patent No.: US 7,787,943 B2
(45) Date of Patent: Aug. 31, 2010

(54) HEART RATE MONITOR FOR SWIMMERS

(76) Inventor: Daniel K McDonough, 242 Carolinian Dr., Summerville, SC (US) 29485

( * ) Notice: Subject to any disclaimer, the term of this patent is extended or adjusted under 35 U.S.C. 154(b) by 237 days.

(21) Appl. No.: 11/828,065

(22) Filed: Jul. 25, 2007

(65) Prior Publication Data
US 2009/0030333 A1 Jan. 29, 2009

(51) Int. Cl.
A61B 5/04 (2006.01)
(52) U.S. Cl. .............. 600/519; 482/55; 482/8; 600/509; 600/372; 600/483; 377/24.2; 434/254
(58) Field of Classification Search .......... 725/10; 600/529, 519, 518, 514, 509, 502, 500, 483, 600/481, 390, 388, 382, 300; 482/3, 8, 11, 482/51, 55; 441/106, 123, 91–96; 428/4–9
See application file for complete search history.

(56) References Cited
U.S. PATENT DOCUMENTS

| 4,681,118 | A | * | 7/1987 | Asai et al. | 600/387 |
| 5,391,080 | A | * | 2/1995 | Bernacki et al. | 434/254 |
| 6,033,228 | A | * | 3/2000 | Ladin | 434/254 |
| 6,580,943 | B2 | * | 6/2003 | Nissila | 600/509 |
| 7,310,549 | B1 | * | 12/2007 | Angelini et al. | 600/509 |
| 2001/0056241 | A1 | * | 12/2001 | Nissila | 600/483 |
| 2003/0126593 | A1 | * | 7/2003 | Mault | 725/10 |
| 2006/0019560 | A1 | * | 1/2006 | Haselsteiner | 441/123 |
| 2006/0098772 | A1 | * | 5/2006 | Reho et al. | 377/24.2 |
| 2006/0142654 | A1 | * | 6/2006 | Rytky | 600/388 |
| 2006/0173370 | A1 | * | 8/2006 | Koivumaa et al. | 600/509 |
| 2007/0293374 | A1 | * | 12/2007 | Chan | 482/55 |

* cited by examiner

Primary Examiner—Carl H Layno
Assistant Examiner—Paula J Stice
(74) Attorney, Agent, or Firm—B. Craig Killough; Ernest B. Lipscomb, III

(57) ABSTRACT

There provided a heart rate monitor that includes a pair of electrodes, a program control panel having a power supply, a vibration feedback module for advising the user when predetermined heart rates have been reached, and a data retrieval member. The electrodes are arranged to be in contact with the swimmer's body and connected to a microcontroller in a program control panel. The program control panel has a plurality of heart rate selection members that provide a signal for sending to the swimmer when the predetermined heart rate has been reached. When the predetermined heart rate is reached, the signal is sent to a vibration feedback module. Another aspect of the present invention is to log heart rate data and swimming duration. This is accomplished by providing the program control panel with blue tooth zone selectors that export data from the program control panel and imports the data to a hand held computer. There are several embodiments of the heart rate monitor described, each of which uses various aspects of a swimsuit depending upon the style and convenience desired by the user.

14 Claims, 6 Drawing Sheets

HEART RATE MONITOR FOR SWIMMERS

BACKGROUND OF THE INVENTION

1. Field of the Invention

The present invention relates to a device to monitor the heartbeat rate of swimmers. More specifically, the present invention is a device that provides feedback to a swimmer indicating if the heart rate is within selected high/low parameters.

2. Description of Related Art

Heart rate monitors are based on measuring heartbeat data. For example, one such device for this purpose is described in U.S. Pat. No. 6,580,943 where there is provided an ECG electrode structure for measuring ECG signs from a person in water. A second measurement electrode is arranged to be in contact only with the water and not with the skin. This device provides heartbeat measurements to a heart rate receiver worn on the user's wrist.

SUMMARY OF THE INVENTION

It is an object of the invention to provide an improved heart rate monitor for swimmers that advises the swimmer when the heart rate is out of a predetermined range.

Another object of the present invention is to provide a device that logs the heart rate and swimming duration of the user and is capable of retrieving that information to a PC or PDA in order to analyze the swimmer's performance.

The objects of the present invention are accomplished by the provision of a heart rate monitor that includes a pair of electrodes, a program control panel having a power supply and a microcontroller, a vibration feedback module for advising the user when predetermined heart rates have been reached, and a data retrieval member.

The electrodes are arranged to be in contact with an area of the swimmer's body such that when in use, the electrodes are electrically insulated from the water and are connected to a program control panel. The program control panel has a power supply and a microcontroller for receiving electrical signals from the electrodes. The program control panel has a plurality of heart rate selection members that provide a signal for sending to the swimmer when the predetermined heart rate has been reached. When the predetermined heart rate is reached, the signal is sent to a vibration feedback module. Another aspect of the present invention is to log heart rate data and swimming duration. This is accomplished by providing the program control panel with blue tooth zone selectors that export data from the microcontroller and import the data to a data retrieval member such as a hand held computer.

There are several embodiments of the heart rate monitor described, each of which uses various aspects of a swimsuit to retain and maintain the electrodes, the program control panel and vibration feedback module in place, depending upon the style and convenience desired by the user.

Other objects, features and advantages of the present invention will become apparent from the following detailed description of the invention taken in conjunction with the accompanying drawings.

BRIEF DESCRIPTION OF THE DRAWINGS

Having described the invention in general terms, reference will now be made to the accompanying drawings, which are not necessarily drawn to scale, and wherein.

DESCRIPTION OF THE PREFERRED EMBODIMENT(S)

The present inventions now will be described more fully hereinafter with reference to the accompanying drawings, in which preferred embodiments of the invention are shown. This invention may, however, be embodied in many different forms and should not be construed as limited to the embodiments set forth herein; rather these embodiments are provided so that this disclosure will be through and complete and will fully convey the scope of the invention to those skilled in the art. Like numbers refer to the elements throughout.

Figure 1:
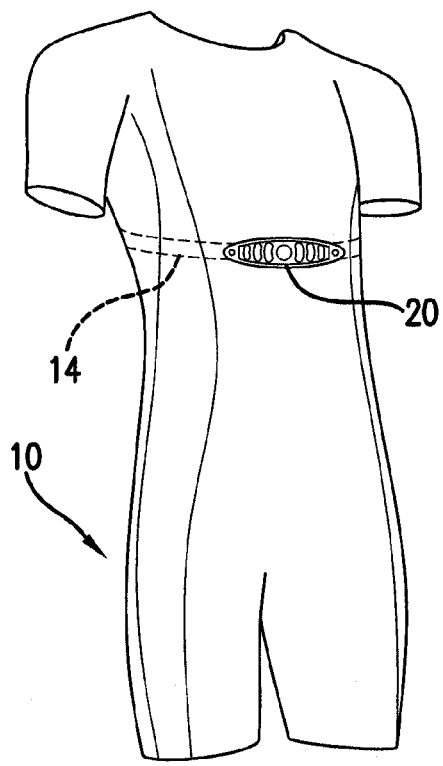
FIG. 1 is a perspective front view of a swimsuit of a first embodiment illustrating the main controller, i.e., elastic belt around the swimmer's chest and showing the program control panel.
Figure 2:
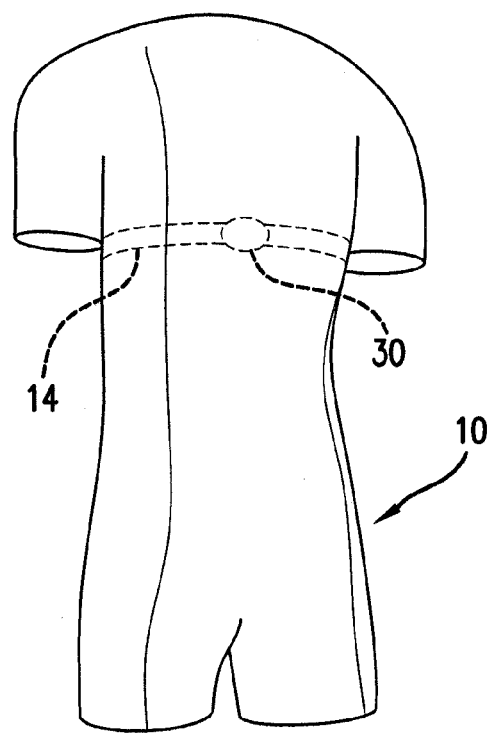
FIG. 2 is a perspective back view of the swimsuit of FIG. 1 illustrating the vibration feedback module.

There are several embodiments of the heart rate monitor but each embodiment includes the basic components of a pair of electrodes providing an electrical signal to a main controller, a power supply, a vibration feedback module and a data retrieval member. Referring now to FIG. 1 there is shown a swimsuit 10 of a first embodiment of the heart monitor. The main controller in the form of program control panel 20 is held in place by adjustable elastic belt 14 worn on the interior of the suit around the swimmer's chest. A pair of electrodes are located on the swimmer's chest. As shown in this embodiment, the program control panel 20 snaps onto the elastic belt 14 through access holes in the swimsuit 10. There is shown in FIG. 2 a back view of swimsuit 10 illustrating the adjustable elastic belt 14 having the vibrating feedback module 30 attached thereto.

Figure 3:
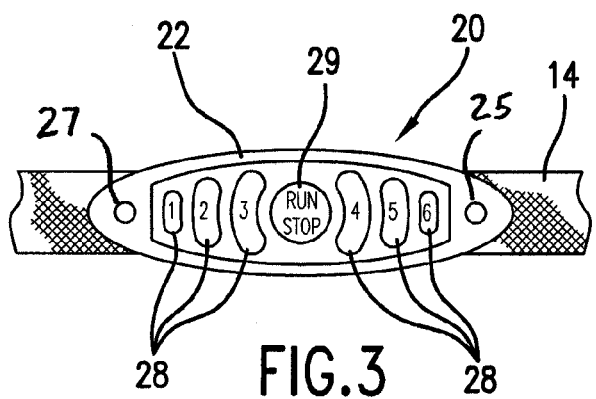
FIG. 3 is a front view of the first embodiment of the program control panel of the present invention.
Figure 4:
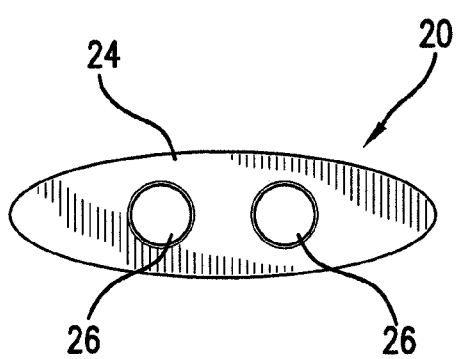
FIG. 4 is a back view of the program control panel shown in FIG. 3.

As shown in FIG. 3, the heart rate monitor includes a program control panel 20 having a main enclosure 22 for housing the electronic components, including a microcontroller, a data memory circuit, a heart rate monitoring circuit and a Bluetooth module. The program control panel 20 may be made of, for example, molded plastic. The front of the program control panel 20 includes keypad having a plurality of buttons. In the embodiment shown, there are a plurality of heart rate selection buttons 28, run/stop button 29 and Bluetooth on/off button 27. The program control panel 20 includes a power supply 26 as shown in FIG. 4 located on the back side 24 of program control panel 20.

Figures 5, 6:
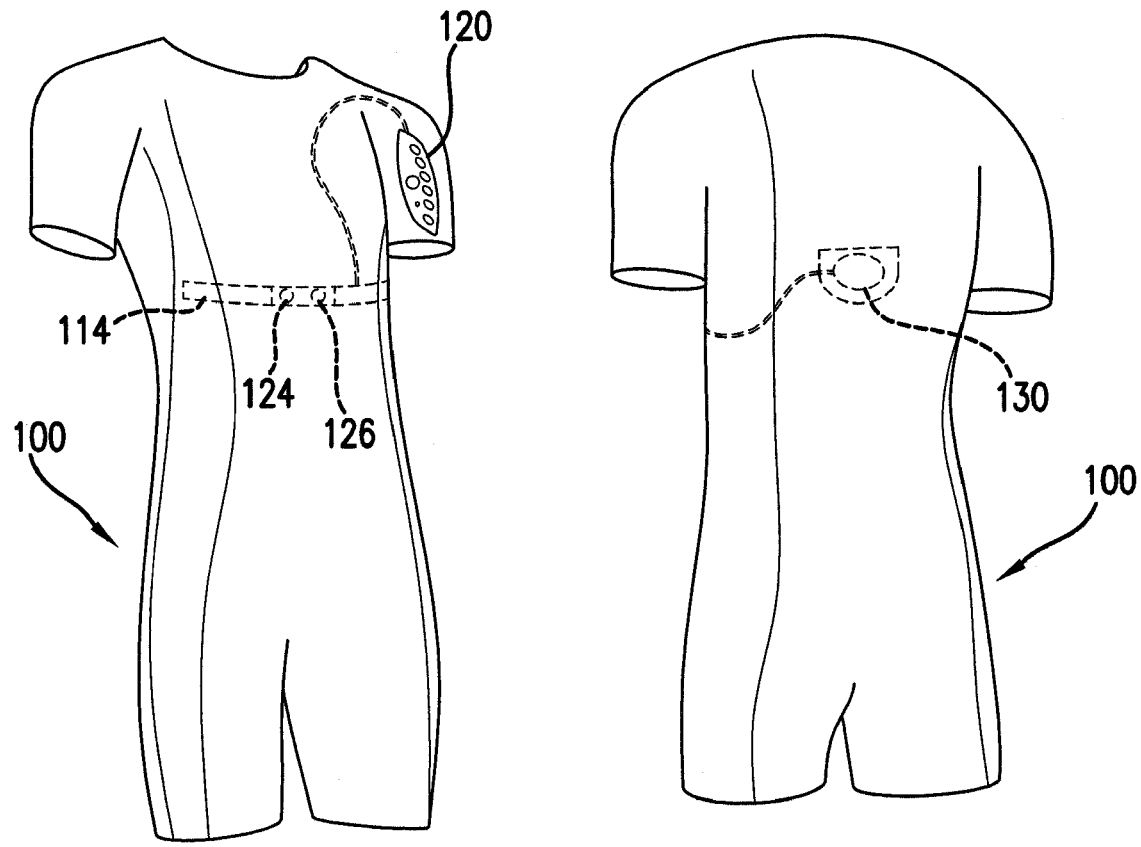
FIG. 5 is a perspective front view of a swimsuit of a second embodiment illustrating the program control panel positioned on the sleeve of the swimsuit.
FIG. 6 is a perspective back view of a swimsuit of the second embodiment similar to that of FIG. 2, illustrating the vibration feedback module.
Figure 7:
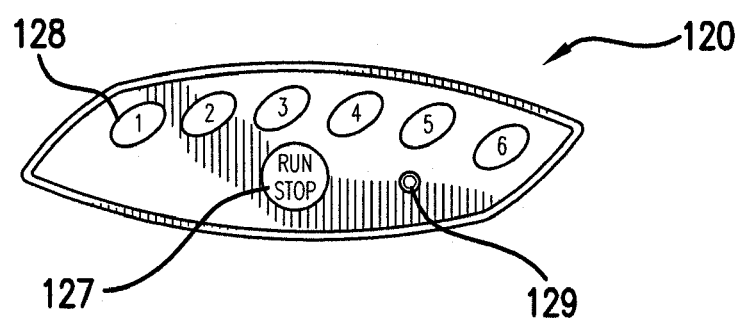
FIG. 7 is a front view of the program control panel of the second embodiment of the present invention.

A second embodiment of the heart rate monitor is shown in FIGS. 5-7. As shown in FIG. 5, there is provided a heart rate monitor strip 114 worn on the interior of the swimsuit 100 at or near the swimmer's chest and held in place by loops or snaps inside the swimsuit 100. A pair of electrodes (not shown) are located on the swimmer's chest and are connected by cable to the program control panel 120. In this embodiment, the program control panel 120 fits into a pocket within the sleeve of the swimsuit and is held fast with snaps or Velcro. There is shown in FIG. 6 a back view of swimsuit 100 illustrating the vibrating feedback module 130 fitted into a sewn pocket inside the swimsuit and wired to the program control panel 120. FIG. 7 illustrates an enlarged view of the front of an embodiment of the program control panel 120 designed especially to be worn on the sleeve. The front of the program control panel 120 includes keypad having a plurality of buttons. In the embodiment shown, there are heart rate selection buttons 128, run/stop button 127 and data send/download button 129. A power supply 124, 126 is located on heart rate monitor strip 114.

Figures 8, 9:
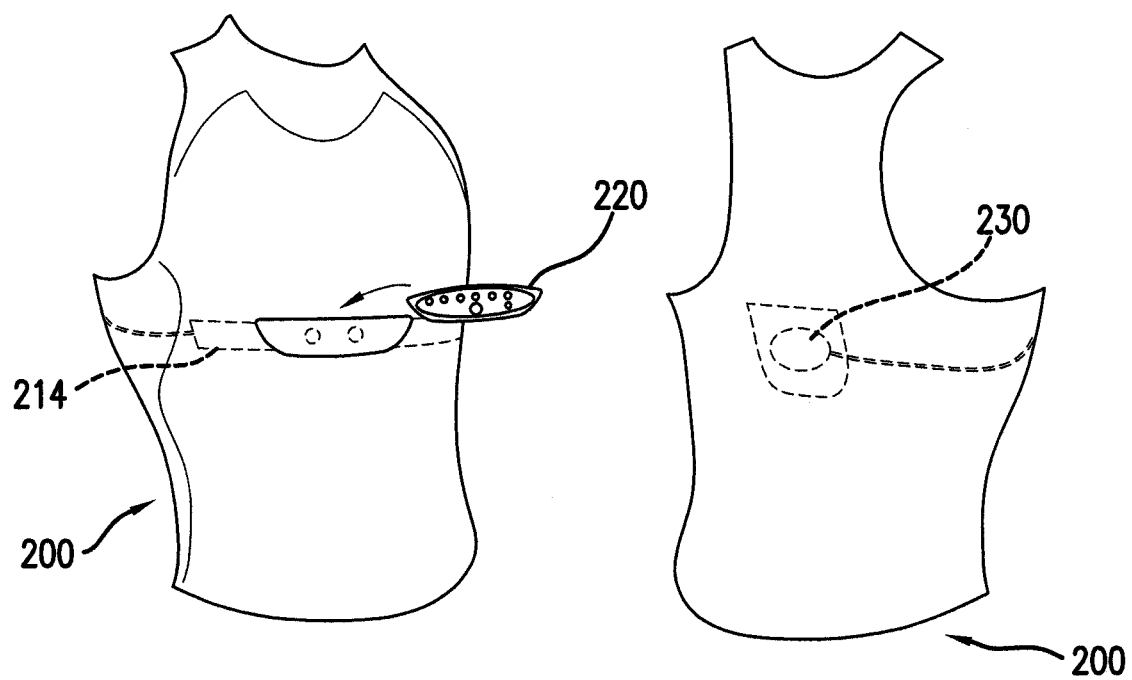
FIG. 8 is a perspective front view of a swimsuit top of a third embodiment illustrating the heart rate monitor program control panel.
FIG. 9 is a perspective back view of a swimsuit top of the third embodiment illustrating a vibrating feedback module.
Figure 10:
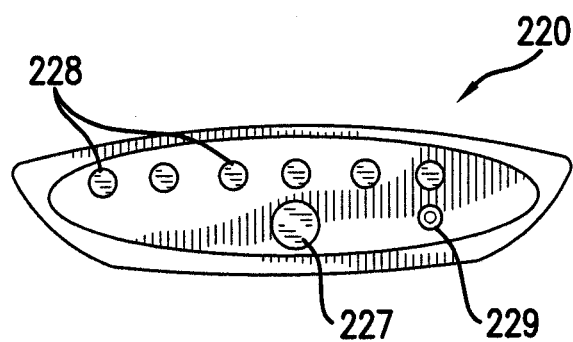
FIG. 10 is a front view of a third embodiment of the program control panel of the present invention.

A third embodiment of the heart rate monitor is shown in FIGS. 8-10. As shown in FIG. 8, there is a heart rate monitor strip 214 worn on the interior of the swimsuit 200 at or near the swimmer's chest. A pocket is provided on the front of the swimsuit and is connected through the suit to the heart rate monitor strip 214. The program control panel 220 fits into a pocket. A pair of electrodes (not shown) are located on the swimmer's chest and are connected by cable to the program control panel 220. There is shown in FIG. 9 a back view of swimsuit 200 illustrating the vibrating feedback module 230 fitted into a sewn pocket inside the swimsuit and wired to the program control panel 220. FIG. 10 illustrates an enlarged view of the front of an embodiment of the program control panel 220 designed especially to be carried in the pocket provided on the front of the swimsuit 200. The front of the program control panel 120 includes keypad having a plurality of buttons. In the embodiment shown, there are heart rate selection buttons 228, run/stop button 227 and data send/download button 229. A power supply (not shown) is also provided.

Figures 11, 12:
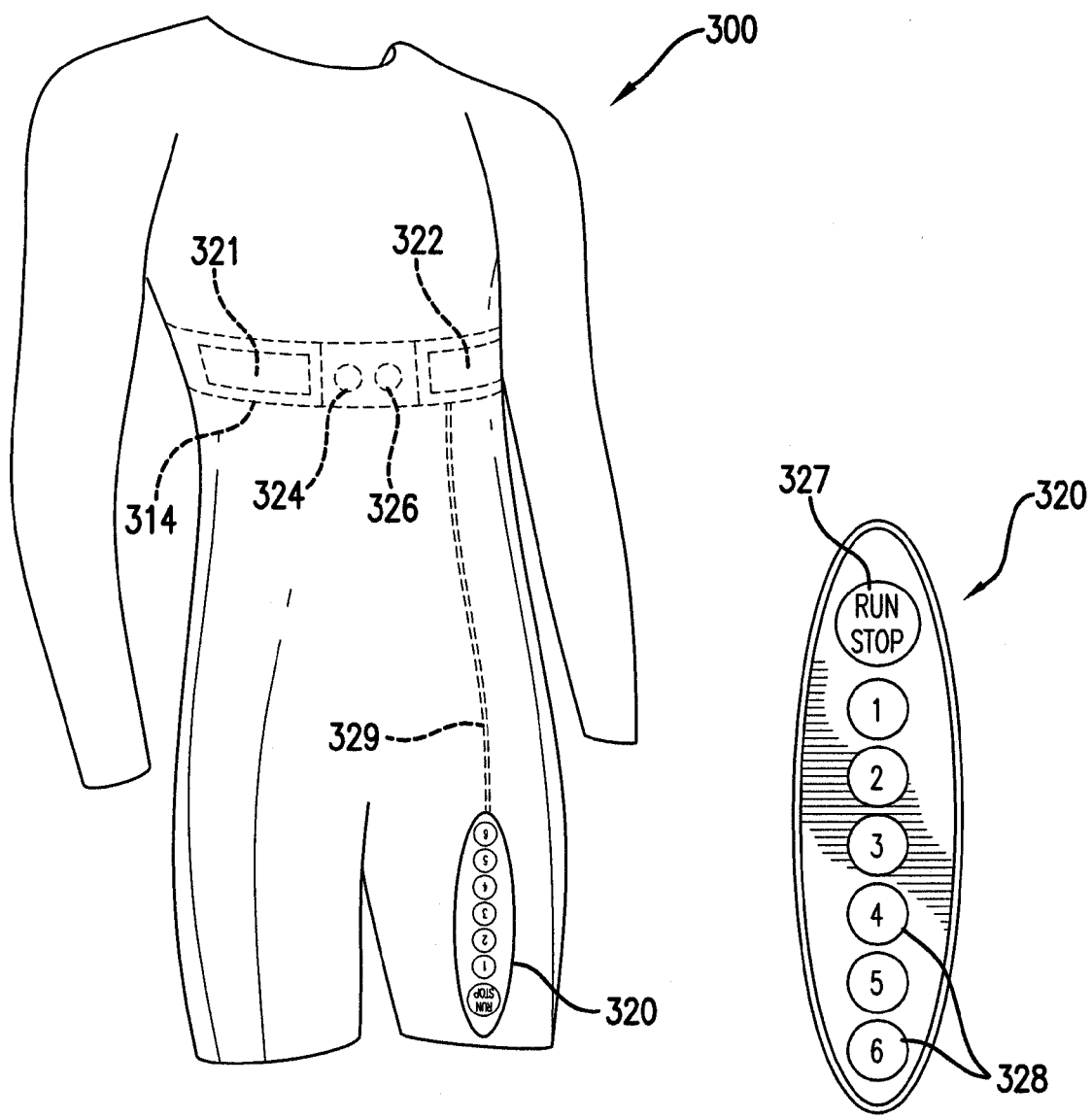
FIG. 11 is a perspective front view of a swimsuit showing a fourth embodiment of the present invention illustrating the program control panel connected to the leg of the a swimsuit.
FIG. 12 is a front view of an embodiment of the program control panel of the present invention designed especially for use with the embodiment shown in FIG. 11.

A fourth embodiment of the heart rate monitor is shown in FIGS. 11-12. As shown in FIG. 11, there is provided a heart rate monitor in the form of an adjustable elastic belt 314 worn on the interior of the swimsuit 300 at or near the swimmer's chest. A power supply, batteries 324, 326, is located on elastic belt 314. A pair of electrodes 321, 322 are attached to the elastic belt 314 located on the swimmer's chest and are connected by cable to the program control panel 320. In this embodiment, the program control panel 320 is sewn into a leg of swimsuit 300. A vibration feedback module 330 is provided at the swimmer's back inside the swimsuit and wired to the program control panel 320. FIG. 12 illustrates an enlarged view of the front of an embodiment of the program control panel 320 designed especially to be worn on the swimmer's leg. The front of the program control panel 320 includes keypad having a plurality of buttons. In the embodiment shown, there are heart rate selection buttons 328 and start/stop button 327.

Figure 13:
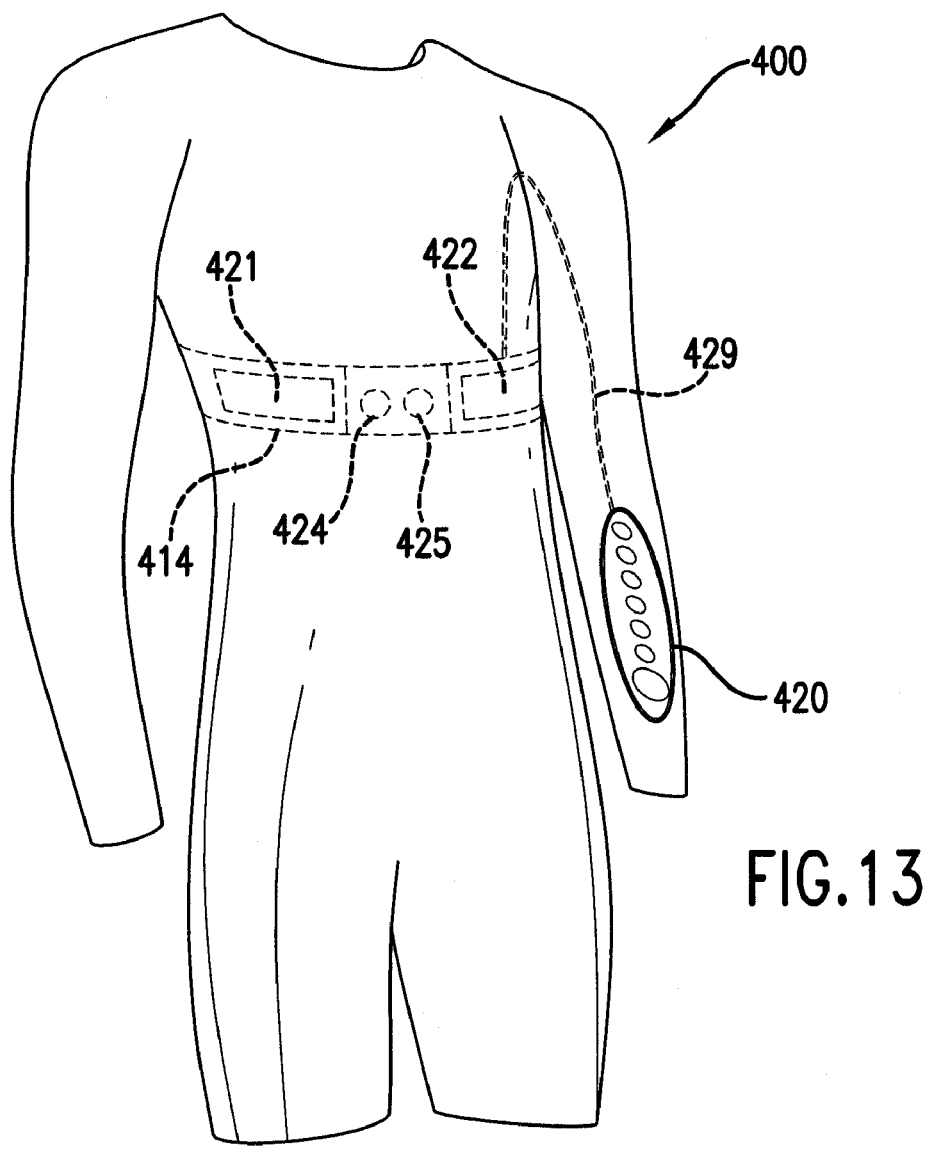
FIG. 13 is a perspective front view of a swimsuit showing an embodiment of the present invention illustrating the program control panel connected to the sleeve of the a swimsuit.
Figure 14:
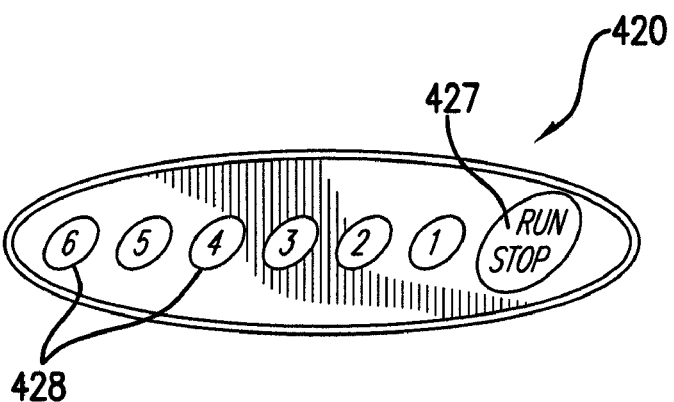
FIG. 14 is a front view of a flexible control panel for use with the embodiment shown in FIG. 13.

A fifth embodiment of the heart rate monitor is shown in FIGS. 13-14. As shown in FIG. 5, there is provided a heart rate monitor in the form of an adjustable elastic belt 414 worn on the interior of the swimsuit 400 at or near the swimmer's chest. A power supply, batteries 424, 426, is located on elastic belt 414. A pair of electrodes 421, 422 are attached to the elastic belt 414 located on the swimmer's chest and are connected by cable to the program control panel 420. In this embodiment, the program control panel 420 is sewn into the sleeve of swimsuit 400. A vibration feedback module is provided at the swimmer's back inside the swimsuit and wired to the program control panel 420. FIG. 14 illustrates an enlarged view of the front of an embodiment of the program control panel 420 designed especially to be worn on the sleeve. The front of the program control panel 420 includes keypad having a plurality of buttons. In the embodiment shown, there are heart rate selection buttons 428 and run/stop button 427.

Figure 15:
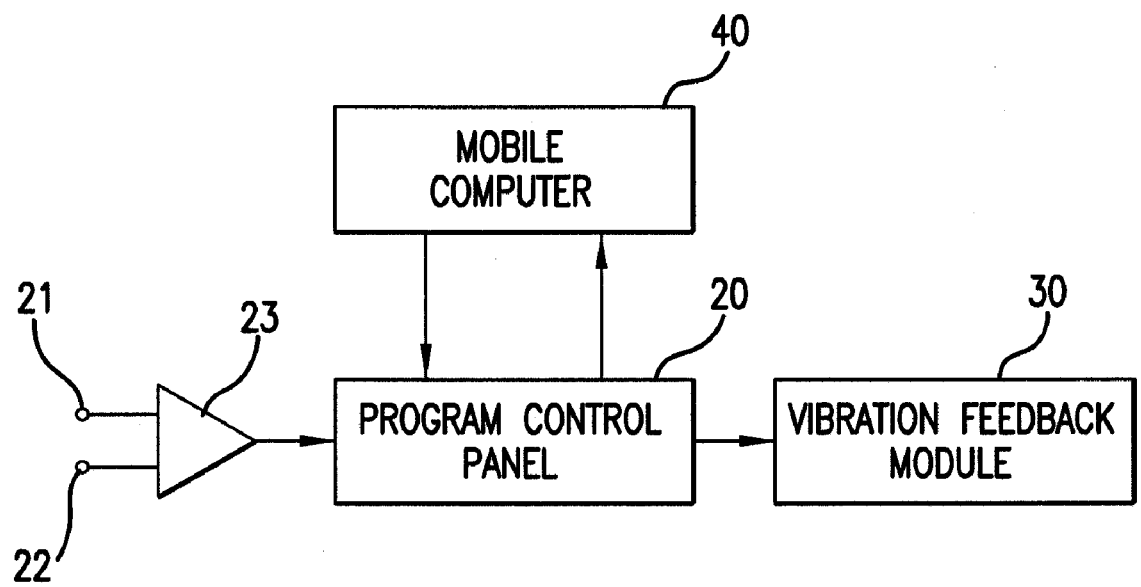
FIG. 15 is a block diagram illustrating operation of the heart rate monitor of the present invention.

As shown in FIG. 15, there is provided a pair of electrodes 21, 22 arranged to be in contact with an area of the swimmer's body to pick up heart ECG signals. The heart rate signal from electrodes 21, 22 is amplified by amplifier 23 and the signal sent via cables or wires to the microcontroller located in the program control panel 20.

The program control panel 20 includes a microcontroller that receives electrical signals from the electrodes. The microcontroller includes a plurality of heart rate selection members that provide a signal when a predetermined heart rate has been reached. One example of a suitable microcontroller that may be used is an Atmel Atmega 164P.

Although there are varying configurations of the face plate of the main closure 22 and functions of the process control panel 20 according to which embodiment of the swimsuit is being used, the operation of each is generally similar. For example, each embodiment of the program control panel has a plurality of heart rate selection buttons, run/stop buttons, and a bluetooth on/off button. A light emitting diode 25 may be used to provide feedback as to the device operation and to report status of heart beat signal.

The program control panel 20 includes a power supply 24, 26 as shown in FIG. 4. In this embodiment lithium batteries are used to power the heart rate monitor. The design uses 1000 mAh 3.6V ½AA battery. The target battery life is 2 months assuming 180 minutes of use per day with one 5 minute Bluetooth session per day, 25% of time the vibrator is active.

The vibration feedback module 30 is connected by cables or wires to the microcontroller for receiving the predetermined signal. Vibration from the vibration feedback module 30 is used to indicate to the swimmer that the heart rate is out of range. The vibration feedback module 30 uses, for example, an off the shelf cell phone vibrator. The heart rate monitor provides feedback to the swimmers indicating if the heart rate is within selected high/low heart rate. The user can select one of a number of programmable heart rate settings 28. When the heart rate is out of the predetermined range a signal is sent to the vibration feedback module 30 to start to vibrate to let the swimmer know that he/she needs to adjust their intensity of exercise.

As shown in FIG. 15, the heart rate monitor uses a wireless interface, such as Bluetooth, to communicate with a mobile computer 40, such as a PC or PDA. Bluetooth implementation emulates a serial port. A standard serial program (such as Hyper-terminal) can be used to exchange information with the microcontroller through a virtual serial communication port. Bluetooth is only used out of water and the device needs to be in a close proximity of the PC or PDA. The device also logs the heart rate and swimming duration. The information can later be retrieved to a PC or a PDA in order to analyze the swimmers performance. The device allows the user to reprogram heart rate settings through PC or PDA. The unit is designed to operate in temperatures from 0 to 60 deg C. The electronic components are enclosed in water proof custom enclosure rated for up to 10 m depth.

Many modifications and other embodiments of the inventions set forth herein will come to mind to one skilled in the art to which these inventions pertain having the benefit of the teachings presented in the foregoing descriptions. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A device for measuring a heart rate of a swimmer comprising:
   a pair of measurement electrodes arranged to be in contact with an area of the swimmer's body to pick up heart rate signals, said electrodes being connected to a program control panel;
   said program control panel held in place in an area of said swimmer's swimsuit, said program control panel comprising;
      a power supply for powering a microcontroller,
      said microcontroller for receiving said heart rate signals from said electrodes and
      a keypad having a plurality of heart rate selection members that are used to set said microcontroller at a predetermined heart rate wherein said microcontroller provides a vibrating signal to a vibration feedback module when said predetermined heart rate has been reached; and
   said vibration feedback module signals said swimmer when said predetermined heart rate has been reached, said vibration module being separate from and located at some other area of the swimmer's swimsuit other than the area of said program control panel.

2. The device according to claim 1 wherein said program control panel further includes a blue tooth module to load settings and off load heart rate logs and a data retrieval member programmed to analyze the swimmer's performance.

3. The device according to claim 1 wherein said program control panel and said vibration feedback module are located separate from each other on an elastic belt around the swimmer's chest.

4. The device according to claim 1 wherein said program control panel is located within a pocket on a sleeve of said swimsuit and said vibration feedback module is fitted into a sewn pocket inside the swimsuit.

5. The device according to claim 1 wherein said program control panel is located within a pocket on the front of said swimsuit and said vibration feedback module fitted into a sewn pocket inside the swimsuit.

6. The device according to claim 1 wherein said program control panel is located on a leg of said swimsuit.

7. The device according to claim 1 wherein said program control panel is located on a sleeve of said swimsuit and said power supply is located on an elastic belt around said swimmer's chest.

8. A device for measuring a heart rate of a swimmer comprising:
   a pair of measurement electrodes arranged to be in contact with an area of the swimmer's body to pick up heart rate signals, said electrodes being connected to a program control panel;
   said program control panel held in place at an area of said swimmer's swimsuit, said program control panel comprising;
      a power supply for powering a microcontroller;
      said microcontroller for receiving said heart rate signals from said electrodes and
      a keypad having a plurality of heart rate selection members that are used to set said microcontroller at a predetermined heart rate wherein said microcontroller provides a vibrating signal to a vibration feedback module when a predetermined heart rate has been reached;
   said vibration feedback module signals said swimmer when said predetermined heart rate has been reached, said vibration module being separate from and located at some other area of the swimmer's swimsuit other than the area of said program control panel;
   a wireless communications module connected to said microcontroller to load settings and off load heart rate logs; and
   a data retrieval member connected to said wireless communications module programmed to analyze the swimmer's performance.

9. The device according to claim 8 wherein said program control panel and said vibration feedback module are located separate from each other on an elastic belt around said swimmer's chest.

10. The device according to claim 8 wherein said program control panel is located within a pocket on a sleeve of said swimsuit and said vibration feedback module is fitted into a sewn pocket inside the swimsuit.

11. The device according to claim 8 wherein said program control panel is located within a pocket on the front of said swimsuit and said vibration feedback module is fitted into a sewn pocket inside the swimsuit.

12. The device according to claim 8 wherein said program control panel is located on a leg of said swimsuit.

13. The device according to claim 8 wherein said program control panel is located on a sleeve of said swimsuit and said power supply is located on an elastic belt around said swimmer's chest.

14. The device according to claim 8 wherein said wireless communications module to load settings and off load heart rate logs is a blue tooth module.

* * * * *